United States Patent [19]

Huber et al.

[11] 4,017,605

[45] Apr. 12, 1977

[54] ACYLATED ORGOTEIN

[75] Inventors: Wolfgang Huber, Atherton; Mark G. Saifer, Berkeley; Lewis D. Williams, Menlo Park, all of Calif.

[73] Assignee: Diagnostic Data, Inc., Mountain View, Calif.

[22] Filed: Sept. 20, 1974

[21] Appl. No.: 507,685

[52] U.S. Cl. .......................... 424/177; 260/112 R; 260/113; 260/115

[51] Int. Cl.$^2$ .......................................... C07G 7/04

[58] Field of Search ............... 260/112 R, 113, 115; 424/177

[56] References Cited

UNITED STATES PATENTS 3,579,495  5/1971  Huber ................................ 260/115

3,637,640  1/1972  Huber ................................ 260/113
3,758,682  9/1973  Huber et al. ....................... 260/113
3,764,711  10/1973  Melnychyn et al. ........ 260/112 R X

OTHER PUBLICATIONS

Chemical Reactions of Polymers, Fettes, 1965, pp. 371–384.

*Primary Examiner*—Howard E. Schain
*Attorney, Agent, or Firm*—Millen & White

[57] ABSTRACT

N-acylated orgotein, although possessing substantially less SODase activity than the native protein, possesses antiinflammatory activity comparable to that of orgotein.

12 Claims, No Drawings

ACYLATED ORGOTEIN

BACKGROUND OF THE INVENTION

This invention relates to orgotein derivatives.

Orgotein is the non-proprietary name assigned by the United States Adopted Name Council to members of a family of water-soluble protein congeners in substantially pure, injectable form, i.e., substantially free from other proteins which are admixed or associated therewith in the sources thereof. U.S. Pat. No. 3,758,682 claims pharmaceutical compositions comprising orgotein.

The orgotein metalloproteins are members of a family of protein congeners having a characteristic combination of physical, chemical, biological and pharmacodynamic properties. Each of these congeners is characterized physically by being the isolated, substantially pure form of a globular, buffer and water-soluble protein having a highly compact native conformation which, although heat labile, is stable to heating for several minutes at 65° C. when dissolved in a buffer solution containing a salt of a divalent metal having an ionic radius of 0.60 to 1.00 A. and which on gel electrophoresis gives a characteristic multiple-band pattern. Chemically, each is characterized by containing all but 0–2 of the protein aminoacids, a small percentage of carbohydrate, no lipids, 0.1 to 1.0% metal content provided by one to 5 gram atoms per mole of one or more chelated divalent metals having an ionic radius of 0.60 to 1.00 A., and substantially no chelated monovalent metals or those that are cell poisons in the molecule.

The aminoacid composition of the orgotein congeners is remarkably consistent irrespective of the source from which it is isolated.

Table I lists the distribution of aminoacid residues, calculated for a molecular weight of 32,500 of several orgotein congeners.

SUMMARY OF THE INVENTION

In a composition aspect, this invention relates to N-acyl orgotein.

In another composition aspect, this invention relates to pharmaceutical compositions comprising the novel acrylated orgoteins of this invention.

In a method of use aspect, this invention relates to the treatment of inflammatory conditions with a composition of this invention.

DETAILED DISCUSSION

The native orgotein protein possesses uniquely high superoxide dismutase activity. See McCord & Fridovich. J. Biol. Chem., 244, 6,049 (1969); Keele, McCord and Fridovich, J. Biol. Chem., 245, 6,176 (1970); ibid, 246, 2,875 (1971). This activity drops precipitously upon acylation of the lysine groups, e.g., to 20–50% of the native protein. Surprisingly, the anti-inflammatory activity of native protein is substantially unaffected by acylation. Accordingly, the acylated protein is useful in the same manner as the native protein for the treatment of inflammatory conditions in mammals and other animals as disclosed in U.S. Pat. No. 3,758,682, whose disclosure is incorporated by reference. The disassociation of anti-inflammatory and SODase activities permits anti-inflammatory therapy with lessened ancillary effects produced by SODase activity.

As stated above, orgotein congeners contain from 20–26 lysine groups. Since the orgotein molecule is made up of two identical peptide chains (sub-units), half of these lysine groups are in each chain, which are tightly but non-covalently bound together under moderate conditions of temperature and pH. Because of the special conformation of the orgotein molecule, usually the $\epsilon$-amino groups of a few lysines in each chain are not titrable with trinitrobenzenesulfonic acid (TNBS) and thus not readily accessible for acylation. However,

TABLE I

AMINO ACID COMPOSITION OF SEVERAL ORGOTEIN CONGENERS
[Residues per mole, M.W. = 32,500]

| Aminoacids | Liver, Beef | Red Blood Cells (RBC) | | | | | | | | | Range |
| --- | --- | --- | --- | --- | --- | --- | --- | --- | --- | --- | --- |
| | | Beef | Sheep | Horse | Pork | Dog | Rabbit | Guinea Pig | Chicken | Human | |
| Alanine | 19 | 19 | 18 | 18 | 18 | 16 | 19 | 22 | 23 | 22 | 16–23 |
| Arginine | 8 | 8 | 10 | 6 | 8 | 8 | 8 | 8 | 8 | 8 | 6–10 |
| Aspartic acid | 37 | 36 | 35 | 35 | 31 | 29 | 34 | 34 | 36 | 37 | 29–34 |
| Cystine-½ | 6 | 6 | 6 | 6 | 6 | 6 | 6 | 4 | 10 | 8 | 4–10 |
| Glutamic acid | 21 | 23 | 22 | 30 | 28 | 30 | 25 | 29 | 26 | 28 | 21–30 |
| Glycine | 53 | 52 | 52 | 51 | 52 | 53 | 54 | 53 | 56 | 51 | 51–56 |
| Histidine | 16 | 16 | 14 | 20 | 16 | 15 | 17 | 15 | 17 | 14 | 14–20 |
| Isoleucine | 18 | 18 | 18 | 14 | 16 | 18 | 16 | 18 | 15 | 17 | 14–18 |
| Leucine | 17 | 17 | 17 | 18 | 16 | 16 | 19 | 17 | 15 | 20 | 15–20 |
| Lysine | 22 | 21 | 23 | 26 | 23 | 20 | 21 | 20 | 21 | 23 | 20–26 |
| Methionine | 2 | 2 | 2 | 2 | 2 | 6 | 3 | 2 | 3 | 1 | 1–6 |
| Phenylalanine | 8 | 8 | 7 | 9 | 8 | 8 | 9 | 8 | 8 | 8 | 7–9 |
| Proline | 12 | 13 | 15 | 10 | 10 | 10 | 13 | 12 | 13 | 12 | 10–15 |
| Serine | 17 | 17 | 14 | 14 | 13 | 20 | 18 | 18 | 15 | 19 | 13–30 |
| Threonine | 26 | 25 | 20 | 16 | 27 | 20 | 21 | 17 | 18 | 18 | 16–27 |
| Tryptophan[1] | Nil | Nil | Nil | Nil | Nil | Nil | Nil | Nil | 1 | 4 | 0–4 |
| Tyrosine[2] | 2 | 2 | 2 | Nil | 4 | 2 | Nil | Nil | 2 | Nil | 0–4 |
| Valine | 33 | 32 | 31 | 29 | 29 | 34 | 31 | 32 | 30 | 30 | 29–33 |
| Total | 317 | 315 | 306 | 304 | 307 | 311 | 315 | 309 | 317 | 320 | 304–310 |

[1]Colorimetric determination
[2]Average of amino acid analysis and spectrophotometric determination.

It can be seen from Table I that orgotein congeners have from 20–26 and usually 20–23 lysine groups, of which all but 1–3 have titrable (with trinitrobenzene sulfonic acid) $\epsilon$-amino groups. The present invention is directed to orgotein derivatives in which at least a portion of the orgotein lysine groups are acylated.

acylation of the non-titrable lysine $\epsilon$-amino groups also can be achieved employing an appropriate acylating agent, e.g., acetic anhydride. The extent of acylation can be determined by the decrease in TNBS-reactive amino groups, taking into account that 1–3 of the lysines of the native orgotein protein are not titrable with TNBS. For example, bovine orgotein assays for only 18 of its 20 to 22 lysines.

Moderate amino group acylation can be quantitated by counting the charge change shown on electrophoresis. However, under normal electrophoresis conditions (pH 8.4 tris-glycine buffer) extensively acylated orgoteins migrate too rapidly for their band pattern to be discerned. This problem can be circumvented by hybridizing the acylated orgotein with native orgotein, as described hereinafter, thereby reducing by one-half the number of acyl groups in the molecule, and subjecting the hybridized molecule to electrophoresis.

Generally speaking, up to about half of the lysines are readily acylated, even with the mildest acrylating agents, e.g., acetylsalicylic acid. All but about one of the accessible (TNBS titrable) lysine groups in each of the orgotein peptide sub-units can be acylated using stronger acylating conditions, e.g., excess acetic anhydride in ice-cold 1M pH 7.5 phosphate buffer.

As would be expected, when less than all of the titrable lysine amino groups are acylated, the distribution of the acyl groups on the orgotein molecule apparently is random since none of the titrable lysine amino groups appear abnormally readily acylable. Because the orgotein molecule is composed of two identical peptide chains, the acyl groups of a partially acylated orgotein will be distributed more or less randomly along each peptide sub-unit but more or less evenly between the two chains. Since a single acylating agent is ordinarily employed, the acyl groups will all be identical. However, it is possible to produce acylated orgoteins having two or more different acyl groups in the molecule and even within each chain thereof.

One way of producing a mixed acyl orgotein is by acylating in stages with different acylating agents. For example, a fraction of the titrable lysine $\epsilon$-amino groups can be acylated with a low concentration of one acylating agent, e.g., $1 \times 10^{-3}$ M acetic anhydride, another fraction of the amino groups acylated with a moderate concentration of another acylating agent, e.g., $5 \times 10^{-3}$ M succinic anhydride, and the remainder of the reactive amino groups acylated with a high concentration of still another acylating agent. What constitutes a low, or high, concentration of acylating agent will depend on the relative rates of reaction with protein amino groups and with solvent and will thus depend on the reaction pH and on the acylating agent, and to a lesser extent on buffer and temperature.

Another method of producing a mixed acyl orgotein is by hybridization. The term hybridization of orgotein refers to the formation of a mixed orgotein from the peptide chains of two different orgotein molecules, e.g., $A_2$ and $B_2$, A and B being their respective peptide chains. ($A_2 + B_2 \rightleftharpoons 2AB$). The charge of the heterodimer, AB, on electrophoresis should be the average of that of the homodimers $A_2$ and $B_2$, assuming that the same portion of each sub-unit is involved in the binding in all cases.

Acetyl orgotein, produced by acylating the native orgotein molecule in 1M pH 7.5 phosphate buffer with excess acetic anhydride, first in ice water for 2.8 hours and then for one hour at room temperature, and succinyl orgotein, produced by succinylating orgotein in 0.1 M pH 7.5 phosphate buffer at room temperature for 3.6 hours, can each be hybridized with native orgotein by heating with a slight excess of native orgotein at 50° C. for 4 hours. The resulting heterodimers electrophorese mainly as one band each, with a charge corresponding to 10 acetyls for the acetyl orgotein/orgotein hybrid and to 9 succinyls for the succinyl orgotein/orgotein hybrid. Since bovine orgotein contains only 10 or 11 lysines/sub-unit, the hybrid products are formed, respectively, from one native orgotein peptide sub-unit plus one acetyl orgotein peptide sub-unit all of whose lysine $\epsilon$-amino groups are acetylamino groups, and from one native orgotein peptide sub-unit plus one succinyl orgotein peptide sub-unit all except one of whose lysine $\epsilon$-amino groups are succinylamino groups.

As will be apparent, these hybride semi-acrylated orgotein molecules can be further acylated with a different acylating agent to produce a hybrid acylated orgotein in which the acyl groups in one peptide chain differ from those in the other.

The N-acyl orgoteins of this invention appear to have essentially the same spacial conformation as the native orgotein molecule. Chelated $CU^{++}$ and $Zn^{++}$ (Gram Atoms Per Mole) contents are about the same as that of orgotein. Like orgotein, they are highly resistant to Pronase an other proteolytic enzymatic degradation. Superoxide dismutase enzymatic (SODase) activity, however, is markedly and increasingly reduced, e.g., to about 20–50% that of orgotein, with increasing degree of acylation, as shown in the table below.

| Avg. No. of N-Acyl Groups | SODase Activity (% of Orgotein) |
|---|---|
| 0 | (100%) |
| 4 N-acetyl | 100 |
| 8 N-acetyl | 80 |
| 11 N-acetyl | 70 |
| 20 N-acetyl | 50 |
| 5 N-succinyl | 60 |
| 17 N-succinyl | 20 |

The exact nature of the N-acyl groups, like the number of N-acyl groups, is not critical as long as it is the acyl radical of a physiologically acceptable acid. Because of the higher molecular weight of the orgotein molecule, even when the orgotein molecule is fully acylated with acyl groups of moderate molecular weight, e.g., RCO— $\leq$ 160, the impact on the overall chemical composition is relatively small, i.e., less than 10%. Of course, the acylation of the free amino groups obviously has a profound impact upon the isoelectric point and resulting electrophoretic mobility but, as discussed hereinbelow, it has no apparent significant effect upon the compact spacial conformation of the molecule and resultant stability, e.g., to heating for one hour at 60° C. and to attack by proteolytic enzymes.

As will be apparent, the acyl group also must be one derived from an acrylating agent capable of acylating an amino group in water or buffer solution, since the reaction is usually conducted therein. Such acylating agents include the free acids in combination with an acylating catalyst such as water-soluble carbodiimides, acid halides, anhydrides, thioesters, ketenes, ketene dimer, enol esters and thioesters, $\alpha$-aminoacid-N-carboxyanhydrides.

More particularly, this invention is directed to N-acyl orgotein wherein the acyl group is that of a mono- or di-basic hydrocarbon carboxylic acid of up to 8 carbon atoms, e.g., of a monobasic alkanoic acid, e.g., formic, acetic, propionic, butyric, isobutyric, $\alpha$-ethylbutyric, valeric, isovaleric, $\alpha$-ethylvaleric, trimethylacetic, 2-methylbutyric, 3-ethylbutyric, hexanoic, diethylacetic, triethylacetic, enanthic, octanoic, of a cyclic acid, preferably a cycloaliphatic acid, e.g., cyclopropylideneacetic, cyclobutylcarboxylic, cyclopentylcarboxylic, cyclopentylacetic, β-cyclopentylpropionic, cyclohexylcarboxylic, cyclohexylacetic, of a carbocyclic aryl or alkaryl acid, e.g., benzoic, 2-, 3- or 4-methylbenzoic, or of a dibasic alkanoic acid, e.g., oxalic, maleic, fumaric, glutaric, α-methylglutaric, β-methylglutaric, β,β-dimethylglutaric, adipic, pimelic and suberic acid.

A preferred class of acyl groups are those of straight or branched chain monobasic alkanoic acids, preferably of 2–8 carbon atoms, e.g., acetyl, propionyl, butyryl, isobutyryl, of which acetyl is most preferred.

Another preferred class of acyl groups are those of a dibasic acid, e.g., alkanoic or aryl acid, especially those capable of forming a cyclic anhydride, e.g., succinic, malonic, glutaric and phthalic, of which succinic is preferred.

Since the exact chemical nature of the acyl radical is not critical, as long as it is not physiologically toxic and it can be formed on the lysine ε-amino groups, contemplated equivalents of the preferred acyl groups described above, insofar as they can be formed, are those of other aliphatic and aromatic unsubstituted and substituted and monobasic, dibasic and polybasic carboxylic acid, saturated or unsaturated aliphatic, araliphatic and aromatic carboxylic acids containing up to 18 and preferably up to 8 carbon atoms, e.g., the acyl radical of undecylic, palmitic, β-cyclohexylpropionic acid, 2,3-, 2,4-, 2,5-, 2,6-, 3,4- and 3,5-dimethylbenzoic, ethylbenzoic, 2,4,6-trimethylbenzoic, cinnamic, napthoic, 3-methyl-α-naphthoic, β-phenylpropionic, diphenylacetic, biphenylacetic or α-naphthylacetic acid, or can be the acyl radical of a carbamic acid, e.g., carbamic acid, phenylcarbamic, n-butylcarbamic, dimethylcarbamic, diethylcarbamic and allophanic acid; or of a heterocyclic acid, e.g., β-furylcarboxylic, pyrrolecarboxylic, β-pyrrolidylpropionic, N-methylpyrrolidyl-2-carboxylic, α-picolinic, nicotinic, indole-2-carboxylic, 6-hydroxyindolyl-3-acetic,and N-methylmorpholyl-2-carboxylic and pyrrolyl-2-carboxylic acid, or of a sulfonic acid of 1–18, preferably 1–12, carbon atoms, including alkanesulfonic, e.g., methane- and ethanesulfonic, and aryl sulfonic, e.g., benzene-and p-toluenesulfonic acid.

Such contemplated equivalents can also be the acyl radical of an acid containing one, two or more simple substituents in the molecule, e.g., hydroxy, halo, alkoxy, acyloxy, sulfonyloxy, amido, sulfato, nitro, mercapto and cyano, in the molecule, e.g., glycolic, lactic, citric, tartaric, d-maleic, d-glyceric, mannoic, gluconic and salicylic acid; of an amino acid, e.g., glycine, aminopropionic, diglycollamic, triglycollamic, methylglycine, dimethylglycine, diethylglycine, para-aminosalicylic, paraaminobenzoic, ethylmercaptoacetic, benzylmercaptoacetic, chloroacetic, fluoroacetic, trichloroacetic, trifluoroacetic, thioglycolic, m-nitrobenzoic, 2,3,4-trimethoxybenzoic, phenoxyacetic and α-naphthoxyacetic acid.

In addition to the N-acetyl "bovine" orgoteins and N-succinyl orgoteins of the examples hereinafter, other examples of N-acyl bovine orgoteins of this invention are N-propionyl orgotein, N-butyryl orgotein, N-benzoyl orgotein, N-o-phthalyl orgotein, wherein in each instance there are 9 such acyl groups in each of the two sub-units of the orgotein molecule and the corresponding orgoteins wherein there are 1, 6 and 10 such acyl groups in each such sub-unit, respectively, and the corresponding human, sheep, horse, pork, dog, rabbit, guinea pig and chicken congeners of each of these.

For uniformity of nomenclature purposes, in naming the acyl groups of the N-acyl orgoteins derived from dibasic acids, divalent radical nomenclature has been used, e.g., succinyl, malonyl, glutaryl and phthalyl. However, as is obvious, the N-acyl group is monovalent and one of the two acyl groups is a free carboxy group so that more precisely the acyl groups are carboxy substituted acyl groups, e.g., β-carboxypropionyl, carboxyacetyl, γ-carboxybutyryl and o-carboxybenzoyl, respectively.

The acylated orgotein can be isolated from the reaction solution, preferably after dialysis to remove extraneous ions, by conventional lyophilization, e.g., in the manner described in U.S. Pat. No. 3,758,682. If desired or necessary, the acylated orgotein can first be purified by ion exchange resin chromatography, electrophoresis and/or gel filtration employing a polymer which acts as a molecular sieve.

Filtration through a micropore filter, e.g., "Millipore", in a conventional manner into sterile vials, optionally after adjusting ionic strength with NaCl and/or sodium phosphate, e.g., to isotonicity, will provide a sterile solution suitable for administration by injection.

The pharamceutical compositions of this invention comprise an N-acyl orgotein of this invention and a pharmaceutically acceptable carrier. The form and character which this carrier takes is, of course, dictated by the mode of administration.

The pharmaceutical composition preferably is in the form of a sterile injectable preparation, for example, as a sterile injectable aqueous solution. The solution can be formulated according to the known art using those carriers mentioned above. The sterile injectable preparation can also be a sterile injectable solution or suspension in a non-toxic parenternally acceptable diluent or solvent, e.g., 1,3-butanediol.

The compositions of this invention combine an effective unit dosage amount of N-acyl orgotein, i.e., the N-acyl orgotein is present at a concentration effective to evoke the desired response when a unit dose of the composition is administered by the route appropriate for the particular pharmaceutical carrier. For example, liquid compositions, both topical and injectable, usually contain about 0.5 to 20 mg. of N-acyl orgotein per 0.25 to 10 cc., preferably about 0.5 to 5 cc., except I.V. infusion solutions, which can also be more dilute, e.g., 0.5 to 20 mg. N-acyl orgotein per 50–1,000 ml., preferably 100–500 ml. of infusion solution. Tablets, capsules and suppositories usually contain 0.1 to 25 mg., preferably 1 to 10 mg., of N-acyl orgotein per unit.

N-acyl orgotein usually is administered by instillation or by injection, e.g., intramuscularaly, subcutaneously, intravenously or intradermally. I.M. is preferred, except in case of shock where I.V. is sometimes preferred for more rapid onset of effect, and in certain localized disorders, e.g., radiation and intersititial cystitis, where local injection is often more effective. Individual doses usually fall within the range of 0.5 to 20 mg. The preferred range for humans is about 0.5 to 4 mg.: for horses, about 5.0–10.0 mg. The exact dosage is not critical and depends on the type and the severity of the disease.

N-acyl orgotein, like orgotein, is effective in treating a wide variety of inflammatory conditions, including those in which synthetic anti-inflammatory agents have limited utility, e.g., because of toxic side effects upon prolonged use.

More specifically, N-acyl orgotein is efficacious in ameliorating inflammatory conditions and mitigating the effects thereof, for instance those involving the urinary tract and the joints, in various mammals. It is useful in alleviating the symptoms of and the structural deformities associated with posttraumatic arthritis, and rheumatoid diseases, such as bursitis, tendonitis, osteoarthritis.

For further details relating to how to isolate the starting orgotein congeners and how to use the N-acyl orgotein of this invention, including modes of administration, dosage forms, dosage regimen and inflammatory and other conditions susceptible to treatment with N-acyl orgotein, see U.S. Pat. No. 3,758,682, whose disclosure is incorporated by reference.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

N-ACETYL ORGOTEIN

EXAMPLE I — With Acetylsalicyclic Acid (aspirin)

Incubation of the native orgotein molecule with aspirin under the conditions outlined below gives a mixture of N-acetylated orgoteins (based on the electrophoresis pattern).

| | pH | Amount | Time | Temp. | No. of N-acetyl groups/orgotein molecule (average by EPG) |
|---|---|---|---|---|---|
| a. | 7.5 | 10 mg/ml | 2 hrs | 37° C | 0.5 |
| b. | 7.5 | 10 mg/ml | 4 hrs | 37° C | 0.8 |
| c. | 7.5 | 10 mg/ml | 20 hrs | 37° C | 1 |
| d. | 7.8 | 5 mg/ml (replenished each day) | 4 days | 37° C | 10–11 |
| e. | 9.0 | 10 mg/ml | 3 hrs | 37° C | 8 |
| f. | 9.0 | 10 mg/ml | 5 hrs | 37° C | 9 |
| g. | 9.0 | 10 mg/ml | 21 hrs | 37° C | 11 |

Up to an average of 11 N-acetyl groups can be introduced by incubation of orgotein with 0.05 M aspirin at pH 9, 37° C. More extensive acetylation can be achieved with larger excesses of aspirin and/or more prolonged reaction times.

EXAMPLE II — With N-Acetylimidazole (NAcIm)

a. 12 mg. orgotein/1 ml. pH 7.5 0.05M borate + 16 mg N-AcIm/2 pH 7.5 0.05M borate; room temperature for 1 hour. Pass through a column of Sephadex G-25 to desalt and terminate reaction. $\Delta OD^{275nm}$ in water equivalent to 0.7 acetylated tyrosines per molecule. Trinitrobenzenesulfonic (TNBS) assay showed 4 residual titrable free amino groups.

b. 12 mg orgotein + 20 mg NAcIm/1ml pH 7.5 0.05M borate; room temperature for 1 hour. Desalt as above. $\Delta OD^{275nm}$ in water equivalent to 0.9 acetylated tyrosines per molecule.

c. 40 mg orgotein (impure sample) + 32 mg NAcIm/1.0 ml, pH 7.5 borate; Room temperature for 1 hour. Desalt as above, $\Delta OD^{275nm}$ in water equivalent to 1.3 to 2.4 acetylated tyrosines per molecule. (Higher value may be due to tyrosine acetylation of impurity.)

d. 25 mg orgotein + 80 mg NAcIm/6 ml of 0.05M pH 7.5 borate; room temperature for 1 hour. Dialyze, lyophilize: yield 21 mg (86% protein by microbiuret) $\Delta OD^{275nm}$ in 7M Guan. HCl equivalent to 1.3 acetylated tyrosines per molecule.

N-acetylation: extensive (electrophoresis)
 1 free amino group left out of 17.5 (TNBS assay)
 Ungar bioassay: fully active
 Metals: $Zn^{++} = 1.8$ $Cu^{++} = 2.1$ gapm
 Electrophoresis: Orgotein = 1.3, AcORG = 16
 SODase Activity: 51% as active as native orgotein in pH 7.5 Cytochrome C assay d. 25 mg orgotein + 80 mg NAcIm/6 ml 0.05M pH 7.5 borate buffer; room temperature for 2 hours. Electrophoresis: ORG = 1.1, AcORG = 13 e. Orgotein + NAcIm/pH 7.5 0.05M borate; room temperature for 3 hours

| NAcIm/Orgotein | TyrOAc/Orgotein (from $OD^{275nm}$) | NAc (by electrophoresis) |
|---|---|---|
| (1) 5 mg/mg | 2.1 mole/mole | 5 mole/mole (average) |
| (2) 10 mg/mg | 1.5 mole/mole | extensive |

EXAMPLE III — With Acetic Anhydride

A. Acetylation at pH 6.2 and 8

Treatment of native orgotein in aqueous buffer with acetic anhydride gives a mixture of N-acetylated orgoteins. The extent of acetylation achieved depends chiefly on the solution pH and on the amount of acetic anhydride added per solution volume, and partially on the buffer and temperature.

| Orgotein | $Ac_2O$ | pH | Temp. | Reaction Time | Degree of Reaction |
|---|---|---|---|---|---|
| 3.44 mg/ml | 3 λ | 6.2, 0.13 M NaOAc | ice-water | 2 hrs | Very little |
| from above | 50 λ | 6.2, 2.02 M NaOAc | 4° | 16 hrs | Some |
| 4.05 mg/ml | 51 λ | 8, pH stat | ice-water | 1 hr | extensive |

B. Successive Acetylation at pH 7.5 and Ice-Water Temperature 1. 0.250 ml of 4.08 mg/ml orgotein solution was diluted with 2.00 ml of water. Acetic anhydride, in 6, 10, 14 and 20λ portions, was added to this orgotein solution with constant stirring. The pH of the reaction was maintained at 7.5 by adding 0.5N NaOH from a 2 ml-Gilmont microburet. When a portion of acetic anhydride was reacted, as indicated by a constant pH at 7.5 (without adding any NaOH), 100λ of the reaction mixture was withdrawn from the bulk, and was added to 1.00 ml of 0.01 M NaOAc to quench any further reaction. This partially acetylated orgotein solution was stored at 4° C for electrophoresis later to determine the degree of acetylation. Electrophorograms (EPGs) of these samples showed that acetylation of the orgotein molecule was almost complete after the first 6λ acetic anhydride in 2.0 ml was consumed.

2. Three 40 mcg/ml orgotein solutions were prepared by adding 10λ 4.08 mg/ml orgotein solution to three vials each containing 1.00 ml of 0.05M, pH 7.5 phosphate buffer. To each of these solutions, 5λ, 10λ or 30λ of 10% $Ac_2O$ in 1,4 dioxane (V/V) was added with vigorous stirring at ice-water temperature. After stirring for 1 hour, each of these reaction mixtures was examined by electrophoresis. Reaction was not complete, as bands of partially acetylated orgotein were evident in all three solutions:

| | Solution | Charge Change | (Acetyl Groups Added) |
|---|---|---|---|
| a) | 5 λ 10% $Ac_2O$ | −7 to −14 | Average 10 |
| b) | 10 λ 10% $Ac_2O$ | −9 to over −14 | Average 12 to 13 |
| c) | 30 λ 10% $Ac_2O$ | −9 to over −14 | Average 12 to 13 |

C. Successive Acetylation at 0° C. and Room Temperature

About 20 mg of orgotein was dissolved in 2 ml of 1M, pH 7.5 phosphate buffer. Acetic anhydride was then added slowly in 40λ portions with stirring at ice-water or room temperature. The pH of the reaction mixture was maintained at 7.5 by adding 6N NaOH from a 2 ml-Gilmont microburet. When the pH of the reaction mixture stopped dropping from 7.5, an indication that the added portion of acetic anhydride had been consumed, the reaction mixture was examined by electrophoresis to determine the extent of acetylation. Usually, a 40λ portion of acetic anhydride would be consumed in 1 to 2 hours at ice-water temperature and in 20 to 60 min. at room temperature, depending upon how much acetic anhydride had been added previously. The acetylation had produced the maximum increase in electrophoretic mobility after about 160λ acetic anhydride was consumed. The reaction product was dialyzed against water then lyophilized.

| | Orgotein | $Ac_2O$ | Reaction Time Ice-water Temp. | Room Temp. | Product Yield |
|---|---|---|---|---|---|
| (1) | 20.5 mg/2 ml | 120 λ | 4.5 hr | — | 16.5 mg/5 ml |
| (2) | 20.5 mg/2 ml | 170 λ | 2.8 hr | 1 hr | 18.35 mg/5 ml |

The properties of acetylated orgotein are summarized below.

Electrophoregram

Protein (amido black) stain: Smeared but relatively narrow band migrating about 17 times farther than native orgotein at pH 8.2.

Enzyme (NBT-Riboflavin) stain: Smeared but relatively narrow band in the same position as the protein band.

TNBS Assay (number of free titrable amino groups)

Example III C(1): 3 amino groups
Example III C(2): 1–2 amino groups

Hydroxamate Assay (number of O-acetyl groups)

Example III C(1): ≤ 2 O-acetyl groups

UV Absorptions

Very similar to those of the native orgotein protein. Comparison of optical density ($OD^{278}$) for acetylated and native orgoteins show that no tyrosine-o-acetyl groups are present in the acetyl orgotein of Examples III C(1) and (2).

Metal Content (by atomic absorption)

$Cu^{++}$ — Example III C(1): 1.85 g-atom/mole
Example III C(2): 2.04 g-atom/mole
$Zn^{++}$ — Example III C(1): 1.73 g-atom/mole
Example III C(2): 1.91 g-atom/mole Dialysis of acetyl orgotein against $2.7 \times 10^{-4}M$ EDTA at pH 7.5 showed that only about 5% of the $Zn^{++}$ and less of the $Cu^{++}$ can be removed from the protein.

Pronase Digestibility

No appreciable change in electropherogram (protein stain) was observed after acetyl orgotein was incubated with pronase at 37° C for 21 hours.

Cytochrome C Assay (SODase activity)

Percent activity of Example III C(1) (based on 100% activity for native orgotein).

| pH 7.5 | pH 10.2 |
|---|---|
| 33 ± 2% | 43 ± 3% |

D. Effect of Phosphate Buffer on Acetylation

Acetylation was carried out in 0.05M, pH 7.5 phosphate and tris-HCl buffers at ice-water and room temperatures. According to electropherograms, there was no appreciable difference in the acetylation reactions in phosphate and tric-HCl buffers at ice-water temperature. At room temperature, acetylation in phosphate buffer was more extensive than that in tris-HCl buffer.

N-SUCCINYL ORGOTEIN

EXAMPLE IV — With Succinic Anhydride at pH 8 and Ice-Water Temperature

| Orgotein | Succinic Anhydride | Reaction Time | Degree of Reaction |
|---|---|---|---|
| 3.80 mg/1.0 ml | 0.77 mg | 1.5 hr | Extensive |
| ¼ of solution from above | 0.37 mg | 1.5 hr | Extensive |

A. Successive Succinylation

The procedure for successive succinylation was similar to that for successive acetylation according to Example III B(1). Reactions were conducted at pH 8 and 7.5. The SODase activity of aliquots of the reaction mixture withdrawn at different stages of reaction was determined by pH 10.2 cytochrome C assay. The percentage activity (based on 100% activity for native orgotein) relative to molar proportion of succinic anhydride added as an ethanolic solution (5.15 mg/ml) to 2.35 ml of an aqueous (5.16 mg/ml) orgotein solution, pH 8, 0° C., is shown below.

| Succinic Anhydride Total Added/ $1.6 \times 10^{-4}$ M Orgotein | SODase Activity % of native Orgotein |
|---|---|
| 0 | (100) |
| $1.1 \times 10^{-3}$ M | 89 |
| $2.7 \times 10^{-3}$ M | 70 |
| $4.9 \times 10^{-3}$ M | 39 |
| $8.2 \times 10^{-3}$ M | 36 |
| $12.8 \times 10^{-3}$ M | 23 |

Following the same procedure but adding the succinic anhydride as a 4.87 mg/ml ethanolic solution to 2.25 ml of a 10.453 mg/ml. aqueous solution of orgotein resulted in a rapid reduction of SODase activity to 60% that of orgotein (after the addition of less than 0.1 ml) followed by a very gradual reduction to about 43% after the addition of 0.6 ml.

B. Succinyl Orgotein

The procedure was the same as that for preparation of acetyl orgotein according to Example III C, except less concentrated (0.1M) pH 7.5 phosphate buffer was used and the succinic anhydride was added in 4 mg (at the beginning of reaction) or 8 mg (toward the end of reaction) portions.

|  | Orgotein | Succinic Anhydride | Reaction Time ice-water temp. | room temp. | Product Yield |
|---|---|---|---|---|---|
| (1) | 20.30 mg/2 ml | 14.93 mg | 5 hrs | — | 17.25 mg/5 ml |
| (2) | 20.7 mg/2 ml | 22.3 mg | — | 3.6 hrs | 18.15 mg/5 ml |

The properties of succinylated orgotein are summarized below.

Electrophoregram

Protein (amido black) stain: Smeared but relatively narrow band migrating toward the (+) pole about 20 × farther than native orgotein at pH 8.2.

Enzyme (NBT-Riboflavin) stain: Smeared but relatively narrow band in the same position as the protein band.

TNBS Assay (number of free titrable $\epsilon$-amino groups)

Example IV B(1): 3 amino groups
Example IV B(2): 3 amino groups

UV Absorption

Very similar to those of the native orgotein protein. Comparison of $OD^{278}$ for succinyl and native orgoteins shows that no tyrosine-O-succinyl groups are present in the succinyl orgoteins.

Metal Content (by atomic absorption)

$Cu^{++}$ — Example IV B(1): 2.04 g-atom/mole
Example IV B(2): 2.37 g-atom/mole
$Zn^{++}$ — Example IV B(1): 1.90 g-atom/mole
Example IV B(2): 2.15 g-atom/mole Dialysis of succinyl orgotein against $2.7 \times 10^{-4}$ EDTA at pH 7.5 showed that only about 5% of the $Zn^{++}$ and less of the $Cu^{++}$ can be removed from the protein.

EXAMPLE V — C-deca(N-acetyl)-orgotein, C-nona(N-succinyl)-orgotein

Hybridization of acetyl orgotein with native orgotein was effected by heating an equimolar mixture of the two proteins in solution at pH 7–8 at 50° for 4 hours. Electrophoresis at pH 8.2 of the resulting hybrid showed that the heterodimer was predominantly one band on electrophoresis with a charge corresponding to 10 acetyls/heterodimer. This partially acetylated orgotein, C-deca(N-acetyl)-orgotein, differs from the partially acetylated orgotein obtained by treatment of orgotein with low concentrations of acetylating agents in that alll the N-acetyl groups are on only one of the two peptide chains, C, comprising the orgotein molecule, rather than distributed randomly over both chains.

Hybridization of succinyl orgotein with native orgotein was effected in a manner similar to that given above for acetyl orgotein. The heterodimer was again predominantly one band on electrophoresis, but with a charge corresponding to 9 succinyls/heterodimer, i.e., C-nona(N-succinyl)-orgotein.

Hybridization of two substituted orgoteins can be done similarly. For example, by heating acetyl orgotein and succinyl orgotein together in solution, one can prepare C-deca(N-acetyl-C'-nona(N-succinyl)-orgotein.

EXAMPLE A

Dissolve dextrose to 5% w/v in a solution of an N-acyl orgotein obtained according to any of Example I-V; sterilize the resulting solution by Millipore micropore filtration; sterile filter into pre-sterilized ampoules or vials under sterile conditions. Thereafter, lyophilize to a sterile powder.

EXAMPLE B

Sterile fill 10 cc. increments of a pure or substantially pure N-acyl orgotein of any of the preceding Examples I–IV in sterile water or sterile isotonic saline solution (0.1 mg/10 ml) directly into sterile rubber stopper vials. Cap and seal the vials. Freeze to store.

EXAMPLE C

Follow the procedure of Example B except sterile lyophilize the contents of the vials prior to capping.

EXAMPLE D

Fifteen parts of an isolated N-acyl orgotein described in one of preceding Examples I-V and thirty parts of sucrose are weighed and mixed. The mixture is dissolved in 30 parts of demineralized water that has been adjusted to pH 9.4 by gaseous ammonia. The solution is then filtered with slight vacuum through an 0.45 $\mu$ pre-wetted Millipore filter. The volume of filtrate is measured and the weight of protein therein calculated as follows: 2 ml. of the filtrate is mixed with 3 ml. Biuret Reagent and the mixture incubated for 15 minutes at 37° C. Absorbance at 555 nm of the mixture is measured against a water (buffer) blank. Concentration in mg/ml. is determined by multiplying absorbance at 555 nm by 8.9.

The aqueous samples are shell-frozen for storage. Lyophilization gives a solid N-acyl orgotein composition which is storage stable at room temperature and which, when reconstituted with water, is free from insoluble denatured protein.

EXAMPLE E

Follow the procedure of Examples A, B, C or D, except add 0.25–0.5% phenol and 0.004–0.01% thimerosal, 0.003–3% methyl paraben, 0.05–0.2% sodium azide or 0.05–0.2% benzyl alcohol to the saline solution as preservative.

EXAMPLE F

To a solution of pure or substantially pure N-acyl orgotein, e.g., produced according to the process of Example III C(2), dissolve sucrose therein to 5% w/v. Sterilize by Millipore filtration and sterile fill into presterilized ampoules or vials in amounts which will provide the desired amount of orgotein per ampoule or vial, e.g., 0.1–5 mg. for a single dose vial an 5–50 mg. for a multi-dose vial. Lyophilize and seal the vials or seal and freeze the solution.

EXAMPLE G

Follow the procedure of Example F but substitute sucrose for the dextrose, in an amount of 1–3 times the weight of the N-acyl orgotein.

EXAMPLE H

Follow the procedure of Exxamples A-F employing 0.1–5 mg. of an N-acyl orgotein of any of Examples I-V, but add 50–150 mg. of the 21-sodium succinate ester of hydrocortisone, 5–25 mg. of the same ester of 6-methylprednisolone, dexamethasone or betamethasone, per 0.2–0.5 mg. of N-acyl orgotein prior to sterilization and lyophilization. Prior to use, these compositions are reconstituted with 1 ml. or more of plain or buffered water per 0.2–0.5 mg. of N-acyl orgotein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. N-acyl orgotein wherein the acyl group is present on at least one lysine $\epsilon$-amino group and is the acyl radical of a mono- or di-basic hydrocarbon carboxylic acid of up to 8 carbon atoms.

2. An N-acyl orgotein of claim 1 wherein the orgotein is bovine.

3. An N-acyl orgotein of claim 1 having at least 10 N-acyl groups per molecule.

4. An N-acyl orgotein of claim 3 wherein the orgotein is bovine.

5. An N-acyl orgotein of claim 1 wherein the acyl radical is alkanoyl of 2–6 carbon atoms.

6. An N-acyl orgotein of claim 1 wherein the acyl radical is acetyl.

7. An N-acyl orgotein of claim 5 wherein the orgotein is bovine.

8. An N-acyl orgotein of claim 5 having at least 10-N-acyl groups per molecule.

9. An N-acyl orgotein of claim 1 wherein the acyl radical is succinyl.

10. An N-acyl orgotein of claim 9 wherein the orgotein is bovine.

11. An N-acyl orgotein of claim 9 having at least 10 N-acyl groups per molecule.

12. A pharmaceutical composition comprising, in admixture with a pharmaceutically acceptable carrier, an anti-inflammatorily effective unit dosage amount of an N-acyl orgotein of claim 1.

* * * * *